(12) United States Patent
Cotrel et al.

(10) Patent No.: US 7,381,724 B2
(45) Date of Patent: *Jun. 3, 2008

(54) OPTICALLY ACTIVE 5H-PYRROLO[3,4-B]PYRAZINE DERIVATIVE, ITS PREPARATION AND PHARMACEUTICAL COMPOSITIONS CONTAINING SAME

(75) Inventors: Claude Cotrel, Paris (FR); Gerard Roussel, Soisy sur Seine (FR)

(73) Assignee: Sepracor Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/416,570

(22) Filed: May 3, 2006

(65) Prior Publication Data

US 2006/0194806 A1    Aug. 31, 2006

Related U.S. Application Data

(60) Continuation of application No. 10/951,844, filed on Sep. 28, 2004, now Pat. No. 7,125,874, which is a continuation of application No. 10/200,510, filed on Jul. 23, 2002, now Pat. No. 6,864,257, which is a division of application No. 09/722,438, filed on Nov. 28, 2000, now Pat. No. 6,444,673, which is a continuation of application No. 09/124,651, filed on Jul. 29, 1998, now Pat. No. 6,319,926, which is a continuation of application No. 08/493,946, filed on Jun. 23, 1995, now abandoned, which is a continuation of application No. 08/342,794, filed on Nov. 21, 1994, now abandoned, which is a continuation of application No. 08/232,313, filed on Apr. 25, 1994, now abandoned, which is a continuation of application No. 08/109,863, filed on Aug. 20, 1993, now abandoned, which is a continuation of application No. 08/034,199, filed on Mar. 19, 1993, now abandoned, which is a continuation of application No. 07/821,662, filed on Jan. 16, 1992, now abandoned.

(30) Foreign Application Priority Data

Jan. 17, 1991  (FR)  .................................. 91 00490

(51) Int. Cl.
C07D 487/04  (2006.01)
A61K 31/4985  (2006.01)
A61P 25/20  (2006.01)

(52) U.S. Cl. ...................................... 514/249; 540/350
(58) Field of Classification Search .................... None
See application file for complete search history.

(56) References Cited

U.S. PATENT DOCUMENTS

| | | | |
|---|---|---|---|
| 3,862,149 A | 1/1975 | Cotrel et al. | 260/268 BQ |
| 4,220,646 A | 9/1980 | Cotrel et al. | 424/250 |
| 4,868,214 A | 9/1989 | Sunshine et al. | 514/568 |
| 4,962,124 A | 10/1990 | Sunshine et al. | 514/568 |
| 5,102,890 A | 4/1992 | Bourzat et al. | 514/299 |
| 5,331,000 A | 7/1994 | Young et al. | 514/570 |
| 5,786,357 A | 7/1998 | Young et al. | |
| 6,319,926 B1 | 11/2001 | Cotrel et al. | |
| 6,436,936 B1 | 8/2002 | Young et al. | |
| 6,444,673 B1 | 9/2002 | Cotrel et al. | |
| 6,864,257 B2 | 3/2005 | Cotrel et al. | |
| 7,125,874 B2 | 10/2006 | Cotrel et al. | |
| 2007/0054914 A1* | 3/2007 | Mandava et al. | 514/249 |
| 2007/0203145 A1* | 8/2007 | Zhu | 514/249 |

FOREIGN PATENT DOCUMENTS

| | | |
|---|---|---|
| EP | 0 495 717 | 7/1992 |
| WO | WO 93/10788 | 6/1993 |

OTHER PUBLICATIONS

H. Tamura, et al, "Chronic Oral Toxicity Study of Zopiclone (27 267 RP) in Beagle Dogs for 6 Months and Recovery Testing After Treatment," *Pharmacometrics*, 26(6): 969-1003 (1983).

Unpublished summary data sheet from IND Serial No. 000, (s)-zopiclone, owned by assignee Sepracor Inc., p. 8-108 (1 page total).

Nair N.P.V., Schwartz G., Dimitri R. et al. A dose-range finding study of zopiclone in insomniac patients. *Intl Clin Psychopharmacol* 1990; 5 (Suppl 2): 1-10.

Martindale. The Extra Pharmacopoeia. The Royal Pharmaceutical Society, London 1996; 31st edition; pp. 743-744.

Houghton G.W., Dennis M.J., Templeton R., Martin B.K., A repeated dose pharmacokinetic study of a new hypnotic agent, zopiclone (Imovane®). *Intl J Clin Pharmacol Therap Toxicol* 1985; 23: 97-100.

(Continued)

*Primary Examiner*—Mark L Berch
(74) *Attorney, Agent, or Firm*—Helsin Rothenberg Farley & Mesiti P.C.

(57) ABSTRACT

Dextrorotatory isomer of 6-(5-chloro-2-pyridyl)-5-[(4-methyl-1-piperazinyl)carbonyloxy]-7-oxo-6,7-dihydro-5H-pyrrolo[3,4-b]pyrazine, its preparation and pharmaceutical compositions containing it which are usable as tranquillisers and hypnotics.

5 Claims, No Drawings

OTHER PUBLICATIONS

Marc-Auréle J., Caille G., Bourgoin J. Comparison of zopiclone pharmacokinetics in patients with impaired renal function and normal subjects. Effects of hemodialysis. *Sleep* 1987; 10 (Suppl 1): 22-26.

Parker G., Roberts C.J.C.. Plasmas concentrations and central nervous system effects of the new hypnotic agent zopiclone in patients with chronic liver disease. *Br J Clin Pharmacol* 1983; 16:259-265.

Viron B., De Meyer M., Le Liboux A. et al., Steady-state pharmacokinetic of zopiclone during multiple oral dosing (7.5 mg nocte) in patients with severe chronic renal failure. *Intl Clin Pysychopharmacol* 1990; 5 (Suppl 2): 95-104.

Sikdar S., Ruben S.M., Zopiclone abuse among polydrug users. *Addition* 1996; 91: 285-286.

Noble S., Langtry H.D., Lamb H.M., Zopiclone. An update of its pharmacology, clinical efficacy and tolerability in the treatment of insomnia. *Drugs* 198; 55:277-302.

Fernandez C., Martin C., Gimenez F., Farinotti. Clinical pharmacokinets of zopiclone, *Clin Pharmacokinet* 1995; 29: 431-441.

Le Liboux Z., Frydman A., Gaillot J., Simultaneous Determination of Zopiclone and its Two Major Metabolites (N-Oxide and N-Dēsmethyl) in Human Biological Fluids by Reversed-Phase High-Performance Liquid Chromatography, *J. Chromatography*, 417: (1987) 151-158.

Musch B. and Maillard F., Zopiclone, The Third Generation Hypnotic: a Clinical Overview, *Intl. Clin. Psychopharmacol.* 5: 147-58 (1990).

Julou L., Blanchard J.C., and Dreyfus J.F., Pharmacological and Clinical Studies of Cyclopyrrolones: Zopiclone and Suriclone, *Pharmacol., Biochem. & Beh.*, 23: 653-659 (1985).

Broadhurst A. and Cushnaghan R.C., Residual effects of Zopiclone (Imovane), *Sleep*, 10 (Suppl. 1): 48-53 (1987).

Anderson A., Zopiclone and Nitrazepam: A Multicenter Placebo Controlled Comparative Study of Efficacy and Tolerance in Insomniac Patients in General Practice, *Sleep*, 10 (Suppl. 1): 54-62 (1987).

Tamminen T. and Hensen P.P., Chronic Administration of Zopiclone and Nitrazepam in the Treatment of Insomnia, *Sleep*, 10 (Suppl. 1): 63-72 (1987).

Inman W., Kubota K., Pearce G., Wilton W., PEM Report No. 10. Zopiclone, *Pharmacoepidemiol Drug Safety* 1993; 2: 499-521.

Doble A., Canton T., Malgouris C., et al. The mechanism of action of zopiclone. *Eur Psychiat* 1995; 10 (Suppl 3): 117s-128s.

Karle J. and Nielsen M., The Mechanism of Action and Pharmacology of Zopiclone, *Rev. Contemp. Pharmacother.*, vol. 9, No. 2, pp. 77-87 (1998).

Richards G., Schoch P., Haefely W., Benzodiazepine receptors: new vistas. *Sem Neurosci* 1991; 3: 191-203.

Doble A., Martin I.L, *The GABA$_A$/benzodiazepine receptor as a target for psychoactive drugs*, RG Landes Company, Austin 1996; pp. 229-264.

Langtry H.D., Benfield P., Zolpidem: A review of its pharmacodynamic and pharmacokinetic properties and therapeutic potential, *Drugs*, 1990; 40: 291-313.

Blanchard J.C., Boireau A., Garret C., Julou L. In vitro and in vivo inhibition by zopiclone of benzodiazepine binding to rodent brain receptors. *Life Sci* 1979; 24: 2417-2420.

Möhler H., Okada T. The benzodiazepine receptor in normal and pathological human brain. *Brit J Psychiat* 1978; 133: 261-268.

Gaillot J., Le Roux Y., Houghton G.W., Dreyfus J.F.. Critical factors for pharmacokinetics of zopiclone ii the elderly and in patients with liver and renal insufficiency. *Sleep* 1987; 10 (Suppl 1): 7-21.

Doble et al., "The Pharmacology of Cyclopyrrolone Derivatives Acting at the GABA$_A$/Benzodiazepine Receptor," *Adv. Biochem. Psychopharmacol.*, 47:407-418 (1992).

Gaillot et al., "Pharmacokinetics and Metabolism of Zopiclone," *Int. Pharmacophysiol.* 17:suppl. 2, pp. 76-91 (1982)/*Pharmacology* 27:suppl. 2, pp. 76-91 (1983).

E.J. Ariens, "Stereoselectivity in Pharmacodynamics and Pharmacokinetics," *Schweiz. Med. Wschr.* 120:131-134 (1990).

Dragstedt, C.A. and Lang, V.F., "Respiratory Stimulants in Acute Cocaine Poisoning in Rabbits," *J. Pharmacol. Ex. Ther.* 32:215-222 (1928).

Litchfield, J.T., Jr., and Wilcoxon, F., "A Simplified Method of Evaluating Dose-Effect Experiments," *J. Pharmacol. and Exp. Therap.* 96:99-113 (1949).

Casarett and Doull's Toxicology: The Basic Science of Poisons, 5th ed. (1996) pp. 21-23.

Prieur, David J. et al., "Procedures for Preclinical Toxicologic Evaluation of Cancer Chemotherapeutic Agents: Protocols of the Laboratory of Toxicology," *Cancer Chemotherapy Reports*, Jan. 1973, part 3, vol. 4, No. 1:1-30.

Everett et al., "Comparative Anticonvulsive Action of 3,5,5-Trimethyloxazolidine-2,4-Dione (Tridone), Dilantin and Phenobarbital," *J. Pharmacol*, 81:402 (1944).

Schwinn et al., "Functional Effects of Activation of Alpha-1 Adrenoceptors by Dexmedetomidine: In Vivo and In Vitro Studies," *J. Pharmacol. & Exp.. Therap.*, 259 (1991).

Marley et al., "Differential Response to Flurazepan in Long-Sleep and Short-Sleep Mice," *Pharmacol, Biochem. & Behav.*, 31:453-58 (1987).

G. Zbinden et al., "Pharmacology of Benzodiazepines: Laboratory and Clinical Correlations," *Advances in Pharmacology*, 5:213-291 (1967).

W.H. DeCamp, "The FDA Perspective on the Development of Stereoisomers," *Chirality*, 1:2-6 (1989).

D.J. Birkett, "Racemates or Enantiomers: Regulatory Approaches," *Clinical and Experimental Pharmacology & Physiology*, 16:479-483 (1989).

R.F. Squires et al., "Benzodiazepine Receptors in Rat Brain," *Nature*, 266:732-734 (1977).

R.E. Study et al., "Cellular Mechanisms of Benzodiazepine Action," *JAMA*, 247:2147-2151 (1982).

D. Nutt, "Selective Ligands for Benzodiazepine Receptors: Recent Developments," *Curr. Aspects Neurosci.*, 2:259-293 (1990).

G. Richards et al., "Role of GABA in the mechanism of benzodiazepine action," *Seminars in Neurosciences*, 3:191-203 (1991).

J.T. Litchfield, "A Method for Rapid Graphic Solution of Time-Percent Effect Curves," *J. Pharmacol. and Exp. Therap.*, 97:399-408 (1949).

G.W. Snedecor et al., Statistical Methods, 7th ed., 149.

Fiche Technique No. 6, J. Pharmacol. and Experim. Therap., 3:407-914 (1970).

E.J. Ariëns, "Racemic Therapeutics—ethical and regulatory aspects," *Eur. J. Clin. Pharmacol.* 41:89-93 (1991).

C. Fernandez et al., "Determination of zopiclone enantiomers in plasma by liquid chromatography using a chiral cellulose carbonate column," *J. Chromatog.*, 572:195-202 (1991).

P. Gauthier et al., "Influence of Zopiclone, a New Generation Hypnotic, on the Intermediate Stage and Paradoxical Sleep in the Rat," *Psychopharcacol.*, 130:139-143 (1997).

Goodman & Gilmans, The Pharmacological Basis of Therapeutics, 8th ed. 346-349 (1990).

C. Malgouris et al., "Autoradiographic Distribution of [3H]-Suridone Binding Sites in the Rat Brain," *Drug Develop. Res.*, 34:336-343 (1995).

A. Doble et al., "The mechanism of action of zopiclone," *Eur. Psychiatry*, 10 Suppl. 3:117s-128s (1995).

J.M. Stutzmann et al., "Pharmacological Properties and Mechanism of Action of the Cyclopyrrolones," *L. Encéphale*, XVIII:393-400 (1992).

V. Bertolasi et al., "Stereochemistry of Benzodiazepine Receptor Ligands. Possible Role of C-H . . . X Interactions in Drug-Receptor Binding and Crystal Structures of CL 218-872, Zopiclone and DMCM", *J. Chem. Soc. Perkin Trans.*, 2:283-289 (1990).

F. Jamali et al., "Enantioselective Aspects of Drug Action and Disposition: Therapeutic Pitfalls," *Journal of Pharmaceutical Sciences*, 78(9):695-715 (1989).

A. Verma and S.H. Snyder, "Peripheral Type Benzodiazepine Receptors", *Annu. Rev. Pharmacol. Toxicol.*, 29:307-322 (1989).

J.P. Brun, "Zopiclone, a Cyclopyrrolone Hypnotic: Review of Properties," *Pharmacology, Biochemistry and Behavior*, 29:831-832 (1988).

P.A. Borea et al., "Stereochemical Features Controlling Binding and Intrinsic Activity Properties of Benzodiazepine-Receptor Ligands", *Molecular Pharmacology*, 31:334-344 (1987).

K.L. Goa and R.C. Heel, "Zopiclone, a Review of its Pharmacodynamic and Pharmacokinetic Properties and Therapeutic Efficacy as an Hypnotic," *Drugs*, 32(1):48-65 (1986).

P. Jacqmin and M. Lesne, "Les Benzodiazepines: Aspects Pharmacodynamiques," *J. Pharm. Belg.*, 40(1):35-54 (1985).

L. Julou et al., "Pharmacological and Clinical Studies of Cyclopyrrolones: Zopiclone and Suricione," *Pharmacology, Biochemistry and Behavior*, 23:653-659 (1985).

H. Kusnierczyk, "Antitumor Activity of Optical Isomers of Cyclophosphamide, Ifosfamide and Trofosfamide as Compared to Clinically Used Racemates," *J. Immunopharm.*, 8(4):455-480 (1986).

F. Jamali, "Pharmacokinetics of enamtiomers of chiral non-steroidal anti-inflammatory drugs," *Eur. J. Drug Metab. and Pharmacokin*, 12(1):1-9 (1988).

D.W. Robertson et al., "Absolute Configurations and Pharmacological Activities of the Optical Isomers of Fluoxetine & Selective Serotonin-Uptake Inhibitor," *J. Med. Chem.*, 31:1412-1417 (1988).

Braestrup C., Squires R.F.. Brain specific benzodiazepine receptors. *Brit J Psychiat* 1978; 133: 249-260.

Garzone P., Kroboth P., Pharmacokinetics of the Newer Benzodiazepines, *Clinical Pharmacokinetics* 16: 337-364 (1989).

Miller L.G., Galpern W.R., Byrnes J.J., and Greenblatt, D.J., Benzodiazepine Receptor Binding of Benzodiazepine Hypnotics: Receptor and Ligand Specificity, *Pharmacology Biochem. And Beh.* vol. 43, pp. 413-416, 1992.

Greenblatt D.J., Divoll M., Abernethy D.R., Ochs H.R., and Shader R.I., Clinical Pharmakokinetics of the Newer Benzodiazepines, *Clin Pharmacokinetics*, 8: 233-252 (1983).

Benavides, J., Peny B., Durand A. et al. Comparative in vivo and in vitro regional selectivity of central ω (benzodiazepine) site ligands in inhibiting [$^3$H]flumazenil binding in the rat central nervous system. *J Pharmacol Exp Therap* 1992; 263: 884-896.

Ankier S.I., Goa K.L., Quazepam: A Preliminary Review of its Pharmacodynamic and Pharmacokinetic Properties, and Therapeutic Efficacy in Insomnia, *Drugs* 35: 42-62 (1988).

Gaillot J., Heusse D., Houghton G.W. et al. Pharmacokinetics and metabolism of zopiclone. *Int Pharmacopysychiat* 1983; 17 (Suppl 2): 76-91.

8$^{th}$ European Cyrstallographic Meeting, 1983 Abstract 1.19P, Bertolasi et al., "Stereochemistry of Benzodiazepine-Receptor Ligands. The Molecular Structure of Zopiclone," 32 (1983).

Shankland et al. "Structural transformations in zopiclone" *Chem. Commun.* 2204-2205 (2001).

Terblanche et al. "Characterization of Zopiclone Crystal Forms Found Among Generic Raw Materials" *Drug Dev. and Indus. Pharm.* 26(5), 531-537 (2000).

Giovannini et al. "Polymorphism and hydration of zopiclone: Determination of crystal structures and, thermodynamic studies as a function of temperature and water vapor pressure" *J. Phys. IV France* 11(Pr10), 93-97 (Dec. 2001).

Jacqmin et al. Selective Affinity of one Enantiomer of Suricone Demonstrated by a Binding Assay with Benzodiazepine Receptors. *Arch. int. Pharmacodyn.* 282, 26-32 (1986).

Codding, P. et al. Structure of Suriclone, a Benzodiazepine Receptor Agonist. *Acta Cryst.* C44, 1938-1942 (1988).

\* cited by examiner

OPTICALLY ACTIVE 5H-PYRROLO[3,4-B]PYRAZINE DERIVATIVE, ITS PREPARATION AND PHARMACEUTICAL COMPOSITIONS CONTAINING SAME

CROSS REFERENCE TO RELATED APPLICATIONS

This application is a continuation of application Ser. No. 10/951,844, filed Sep. 28, 2004, now U.S. Pat. No. 7,125,874, which is a continuation of application Ser. No. 10/200,510, filed Jul. 23, 2002, now U.S. Pat. No. 6,864,257, which is a divisional of application Ser. No. 09/722,438, filed Nov. 28, 2000, now U.S. Pat. No. 6,444,673, which is a continuation of application Ser. No. 09/124,651, filed Jul. 29, 1998, now U.S. Pat. No. 6,319,926, which is a continuation of application Ser. No. 08/493,946, filed Jun. 23, 1995 (abandoned), which is a continuation of application Ser. No. 08/342,794, filed Nov. 21, 1994 (abandoned), which is a continuation of application Ser. No. 08/232,313, filed Apr. 25, 1994 (abandoned), which is a continuation of application Ser. No. 08/109,863, filed Aug. 20, 1993 (abandoned), which is a continuation of application Ser. No. 08/034,199, filed Mar. 19, 1993 (abandoned), which is a continuation of application Ser. No. 07/821,662, filed Jan. 16, 1992 (abandoned). U.S. Ser. No. 07/821,662 claimed the priority of French application 91 00490, filed Jan. 17, 1991. The entire contents of each of the prior applications are incorporated herein by reference.

In French Patent FR 72/00,505, published under number 2,166,314, a description was given, in particular, of 6-(5-chloro-2-pyridyl)-5-[(4-methyl-1-piperazinyl)carbonyloxy]-7-oxo-6,7-dihydro-5H-pyrrolo[3,4-b]pyrazine, also known by the name of zopiclone, which is a noteworthy hypnotic product.

As a result of the presence of an asymmetric carbon atom at the 5-position of the 5H-pyrrolo[3,4-b]-pyrazine ring-system, zopiclone must be considered, in racemic form, to consist of a strictly equimolecular mixture of the laevorotatory and dextrorotatory forms.

It has now been found, and this forms the subject of the present invention, that the dextrorotatory isomer of zopiclone possesses properties which are not obvious in the light of those of racemic zopiclone.

The subject of the present invention is hence the dextrorotatory isomer of zopiclone, its preparation and pharmaceutical compositions containing it. In a racemic product, it is known that, often, one of the two enantiomers is active and that an enhancement of the toxicity may be linked to this activity, the other enantiomer being both markedly less active or inactive and less toxic. For such products, the gain in activity does not compensate for the drawbacks due to an enhanced toxicity.

In the case of zopiclone, it was found, surprisingly and unexpectedly, not only that the dextrorotatory isomer is approximately twice as active as the racemate while having a lower toxicity than that of the racemate, but that the laevorotatory isomer is both almost inactive and more toxic than the racemate.

For example, when administered orally to mice, zopiclone possesses a toxicity ($LD_50$) in the region of 850 mg/kg, whereas the dextrorotatory isomer has a toxicity in the region of 1.5 g/kg and the laevorotatory isomer possesses an $LD_50$ of between 300 and 900 mg/kg.

In animals, the dextrorotatory isomer of zopiclone displays hypnotic, sedative, anxiolytic, muscle-relaxant and anticonvulsant properties.

From the standpoint of the potency of action in the main tests demonstrating the tranquillising and hypnotic activity of zopiclone, such as the test of affinity for central benzodiazepine receptor sites according to the technique of J. C. Blanchard and L. Julou, J. of Neurochemistry, 40, 601 (1983) based on the work of Squires and Braestrup, Nature, 266, 732-734 (1977), or the test of antagonist activity with respect to pentetrazol-induced convulsions according to the technique of Everett and Richards, J. Pharmacol., 81, 402 (1944), or in the writhing reflex test in mice according to the technique of Zbinden and Randall, Advances in Pharmacology 5, 213-291 (1967), the dextrorotatory isomer is approximately twice as active whereas the laevorotatory isomer is almost inactive.

According to the invention, the dextrorotatory isomer of zopiclone may be prepared from the corresponding racemate according to the usual methods, such as chiral-phase chromatography, resolution of an optically active salt, stereoselective enzymatic catalysis by means of an appropriate microorganism, or asymmetric synthesis.

More especially, the dextrorotatory isomer of zopiclone may be obtained by resolution of zopiclone by means of an optically active acid, working in an appropriate organic solvent.

As an optically active acid which is especially suitable, D(+)-O,O'-dibenzoyltartaric acid may be mentioned.

Generally, the reaction is performed in an organic solvent chosen from halogenated aliphatic hydrocarbons such as dichloromethane and nitriles such as acetonitrile, taken alone or mixed.

By working in this manner, the salt of the dextrorotatory isomer precipitates and the laevorotatory isomer is extracted from the mother liquors of crystallisation.

The dextrorotatory isomer of zopiclone is displaced from its salt by means of a base such as sodium hydroxide.

The dextrorotatory isomer of zopiclone is useful in humans for the treatment of states due to a dysfunction of the central nervous system.

The dextrorotatory isomer of zopiclone is, e.g., useful as a hypnosedative, tranquilliser, muscle relaxant and anticonvulsant.

However, the dextrorotatory isomer of zopiclone is more especially useful in man as a hypnotic.

Since it acts on the various parameters of sleep, the dextrorotatory isomer of zopiclone increases sleeptime and improves sleep quality, and decreases the number of episodes of waking at night and of early morning awakening.

The present invention relates to pharmaceutical compositions containing the dextrorotatory isomer of zopiclone or one of its pharmaceutically acceptable salts, in the pure state or in the presence of a diluent or a coating. These compositions may be employed orally, rectally or parenterally.

As pharmaceutically acceptable salts, salts of inorganic acids (such as hydrochlorides, sulphates, nitrates, phosphates) or organic acids (such as the acetates, propionates, succinates, benzoates, fumarates, tartrates, theophyllineacetates, salicylates, phenolphthalinates, methylenebis (β-hydroxynaphthoates), or of substitution derivatives of these acids, may be mentioned.

As solid compositions for oral administration, tablets, pills, powders or granules may be used. In these compositions, the active product according to the invention is mixed with one or more inert diluents such as sucrose, lactose or starch. These compositions can also comprise substances other than diluents, e.g. a lubricant such as magnesium stearate.

As liquid compositions for oral administration, solutions, suspensions, syrups, elixirs and pharmaceutically acceptable emulsions, containing inert diluents such as water or liquid paraffin, may be used. These compositions can also comprise substances other than diluents, e.g. wetting, sweetening or flavouring products.

The compositions for parenteral administration can be suspensions, emulsions or aqueous or non-aqueous, sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilisation may be carried out in several ways, e.g. using a bacteriological filter, by incorporating sterilising agents in the composition, by irradiation or by heating. They may be prepared in the form of sterile compositions which can be dissolved at the time of use in sterile water or any other sterile injectable medium.

The compositions for rectal administration are suppositories which can contain, apart from the active product, excipients such as cocoa butter.

In human therapy, the doses depend on the effect sought and the treatment period; taken orally, they are generally between 2.5 and 15 mg per day for an adult.

The examples which follow, given without implied limitation, illustrate the present invention.

EXAMPLE 1

A solution of zopiclone (23.28 g; 0.06 mol) in dichloromethane (300 cc) is added to a solution of D(+)-O,O'-dibenzoyltartaric acid in the form of a monohydrate (22.56 g; 0.06 mol) in dichloromethane (300 cc). The reaction mixture is concentrated to dryness under reduced pressure. The crude salt obtained is recrystallised in acetonitrile (2000 cc) to give, in a 46% yield, a crystallised product (21.3 g), m.p. 160-165° C. (with decomposition), the optical rotation of which is $[\alpha]_D^{20}=83°$ (c=0.5; acetone).

The product obtained is dissolved in dichloromethane (180 cc) under reflux. Acetonitrile (200 cc) is added and the mixture is left standing for 1 hour at a temperature of 5° C. The crystallised product obtained is recrystallised again under the same conditions. A crystallised salt (16.5 g), m.p. 160-165° C. (with decomposition), the optical rotation of which is $[\alpha]_D^{20}=102°$ (c=0.5; acetone), is thereby obtained in a 36% yield.

The salt thereby obtained is dissolved in water (125 cc) in the presence of dichloromethane (125 cc). The mixture is alkalinised to pH 11 by slowly adding 2N aqueous sodium hydroxide solution. After settling has taken place, the aqueous phase is separated and extracted twice with dichloromethane. The combined organic phases are washed with water and then dried over magnesium sulphate. After filtration, evaporation of the solvent and recrystallisation of the product obtained in acetonitrile (80 cc), the dextrorotatory isomer (5.4 g) of zopiclone, m.p. 206.5° C., the optical rotation of which is $[\alpha]_D^{20}=135°\pm3°$ (c=1.0; acetone), is obtained in a 23% yield.

The mother liquors of crystallisation of the salt of zopiclone with D(+)-O,O'-dibenzoyltartaric acid are concentrated to dryness under reduced pressure to give a salt (22.05 g) the optical rotation of which is $[\alpha]_D^{20}=-21°$ (c=0.2; acetone).

The salt thereby obtained is dissolved in water (125 cc) in the presence of dichloromethane (125 cc). The mixture is alkalinised to pH 11 by slowly adding 2N aqueous sodium hydroxide solution. After settling has taken place, the aqueous phase is separated and extracted twice with dichloromethane. The combined organic phases are washed with water and then dried over magnesium sulphate. After filtration and evaporation of the solvent, the crystallised solid obtained (8.45 g) is recrystallised in acetonitrile (successively 100, 50 and 45 cc). The laevorotatory isomer (3.13 g) of zopiclone, m.p. 206.9° C., the optical rotation of which is $[\alpha]_D^{20}=-133°\pm3°$ (c=1.0; acetone), is thereby obtained in a 13.9% yield.

EXAMPLE 2

Tablets containing 3 mg of active product and having the following composition are prepared according to the usual technique:

| | |
|---|---|
| dextrorotatory isomer of zopiclone | 0.003 g |
| starch | 0.100 g |
| precipitated silica | 0.035 g |
| magnesium stearate | 0.005 g |

The invention claimed is:

1. A mixture of isomers of 6-(5-chloro-2-pyridyl)-5-[(4-methyl-1-piperazinyl)carbonyl-oxy]-7-oxo-6,7-dihydro-5H-pyrrolo[3,4-b]pyrazine, wherein the mixture has an optical rotation $[\alpha]_D^{20}$ of $135°\pm3°$ when measured at 1.0 g/100 mL in acetone.

2. A pharmaceutical composition comprising the mixture of claim 1 and one or more pharmaceutically acceptable diluents, coatings, lubricants, wetting products, sweetening products, flavouring products, solvents, vehicles or adjuvants.

3. The pharmaceutical composition of claim 2 that is in the form of a tablet, pill, powder or granule.

4. The pharmaceutical composition of claim 2 that is in the form of a tablet.

5. A method of inducing an effect selected from the group consisting of a hypnotic effect, a sedative effect and a tranquilizing effect, comprising administering to a human in need thereof an effective amount of the mixture of claim 1.

* * * * *